US005682526A

United States Patent [19]
Smokoff et al.

[11] Patent Number: 5,682,526
[45] Date of Patent: Oct. 28, 1997

[54] METHOD AND SYSTEM FOR FLEXIBLY ORGANIZING, RECORDING, AND DISPLAYING MEDICAL PATIENT CARE INFORMATION USING FIELDS IN A FLOWSHEET

[75] Inventors: Timothy L. Smokoff, Renton; Tom Marlin, Edmonds, both of Wash.; Herbert J. Uhrig, Duluth, Ga.

[73] Assignee: SpaceLabs Medical, Inc., Redmond, Wash.

[21] Appl. No.: 504,801

[22] Filed: Jul. 20, 1995

[51] Int. Cl.[6] .................................................... G06F 17/30
[52] U.S. Cl. ........................ 395/615; 395/602; 395/611; 128/710
[58] Field of Search ....................... 364/413.01; 395/161, 395/600, 700, 608, 764, 768, 601, 603, 765, 202; 340/172.5; 128/710

[56] References Cited

U.S. PATENT DOCUMENTS

| | | | |
|---|---|---|---|
| 3,872,448 | 3/1975 | Mitchell, Jr. | 340/172.5 |
| 4,878,175 | 10/1989 | Norden-Paul et al. | 364/413.01 |
| 5,077,666 | 12/1991 | Brimm et al. | 364/413.02 |
| 5,247,611 | 9/1993 | Norden-Paul et al. | 395/161 |
| 5,253,361 | 10/1993 | Thurman et al. | 395/603 |
| 5,253,362 | 10/1993 | Nolan et al. | 395/601 |
| 5,301,319 | 4/1994 | Thurman et al. | 395/600 |
| 5,307,262 | 4/1994 | Ertel | 364/413.01 |
| 5,325,478 | 6/1994 | Shelton et al. | 395/768 |
| 5,337,405 | 8/1994 | Lindauer | 395/764 |
| 5,410,704 | 4/1995 | Norden-Paul et al. | 395/700 |
| 5,482,050 | 1/1996 | Smokoff et al. | 128/710 |
| 5,546,580 | 8/1996 | Seliger et al. | 395/600 |
| 5,592,945 | 1/1997 | Fiedler | 128/710 |

OTHER PUBLICATIONS

"System Administrator Guide," SpaceLabs Medical, Inc. PC Chartmaster, 1994.

"Operations Manual," SpaceLabs Medical Inc., PC Chartmaster, 1994.

Fackler et al. "Integration of Intermittent Clinical Data with Continuous Data from Bedside Monitors", Computer–Based Medical Systems, 1993 Symposium, pp. 289–294.

Petroni et al. "An Automatic Speech Recognition System for Bedside Data Entry in an Intensive Care Unit", Circuits and Systems, 1990 IEEE Midwest Symposium, pp. 791–794.

Saab et al. "Data Modeling and Design of a Patient Data Management System in an Intensive Care Unit", Computer Based Medical Systems, 1992 Symposium, May 1992, pp. 54–63.

Primary Examiner—Thomas G. Black
Assistant Examiner—Charles L. Rones
Attorney, Agent, or Firm—Seed and Berry LLP

[57] ABSTRACT

A method and system for flexibly organizing, recording, and displaying medical patient care information is provided. In a preferred embodiment, a patient information management facility enables users to customize a patient information hierarchy, which defines and organizes the information that may be stored about each patient, as well as patient data flowsheets, which define views in which the patient data stored according to the hierarchy may be entered and viewed, in a way that is optimized for the structure and procedures of the particular health care organization. The facility enables users to add, modify, and rearrange global or local patient information parameters that make up the hierarchy. Users may define the parameters to be any of a number of types. The user may also customize flowsheets used for entering and displaying result values of parameters defined in the hierarchy for particular patients. The user may expand and contract overview encapsulating parameters to display or hide the encapsulated parameters encapsulated therein. The facility also allows the user to link a result value of one parameter to other parameters, causing the linked-to parameters to be displayed when the result value is entered.

25 Claims, 21 Drawing Sheets

| parameter id | parameter name | linked from parameter | parameter data type | normal value | data type - specific information |
|---|---|---|---|---|---|
| 10001 | cough | yes | select | none | none non-productive productive 10013, 10014 |
| 10002 | respiration | no | select | normal | normal heavy shallow |
| 10003 | chest sounds | no | select | none | none soft loud |
| 10004 | sleep | no | select | | awake asleep |
| 10005 | Demerol | no | encapsulating | | 10007, 10008, 1009 |
| 10006 | Amoxicillin | no | encapsulating | | 10010, 10011, 10012 |
| 10007 | dose | no | integer | | |
| 10008 | dose units | no | select | cc | mg cc |
| 10009 | route | no | select | intravenous | oral intravenous |
| 10010 | dose | no | integer | | |
| 10011 | dose units | no | select | mg | mg cc |
| 10012 | route | no | select | oral | oral intravenous |
| 10013 | sputum color | no | select | | white yellow green |
| 10014 | sputum amount | no | select | | white yellow green | parameter definition table 400
401 402 403 404 405 406

FIG. 4 parameter definition table 400

| parameter id 401 | parameter name 402 | linked from parameter 403 | parameter data type 404 | normal value 405 | data type - specific information 406 |
|---|---|---|---|---|---|
| 10001 | cough | yes | select | none | none<br>non-productive<br>productive  10013, 10014 |
| 10002 | respiration | no | select | normal | normal<br>heavy<br>shallow |
| 10003 | chest sounds | no | select | none | none<br>soft<br>loud |
| 10004 | sleep | no | select | | awake<br>asleep |
| 10005 | Demerol | no | encapsulating | | *10007, 10008, 1009 |
| 10006 | Amoxicillin | no | encapsulating | | *10010, 10011, 10012 |
| 10007 | dose | no | integer | | |
| 10008 | dose units | no | select | cc | mg<br>cc |
| 10009 | route | no | select | intravenous | oral<br>intravenous |
| 10010 | dose | no | integer | | |
| 10011 | dose units | no | select | mg | mg<br>cc |
| 10012 | route | no | select | oral | oral<br>intravenous |
| 10013 | sputum color | no | select | | white<br>yellow<br>green |
| 10014 | sputum amount | no | select | | white<br>yellow<br>green |
| ... | | | | | |

FIG. 7 result table 700

| | patient i.d. 701 | parameter i.d. 702 | result time 703 | result value 704 |
|---|---|---|---|---|
| 11 | 100001 | 10001 | 01/25 23:00 | none |
| 12 | 100001 | 10003 | 01/25 23:00 | soft |
| 13 | 100002 | 10001 | 01/25 23:00 | non-productive |
| 14 | 100002 | 10001 | 01/26 00:00 | productive |
| 15 | 100002 | 10004 | 01/25 23:00 | asleep |
| 16 | 100002 | 10004 | 01/26 00:00 | asleep |
| 17 | 100003 | 10007 | 01/26 00:00 | 100 |
| 18 | 100003 | 10008 | 01/26 00:00 | mg |
| ... | | | | |

FIG. 8

| | 01/25 23:00 | 01/26 00:00 | 01/26 01:00 | 01/26 02:00 | 01/26 03:00 |
|---|---|---|---|---|---|
| cough | none | | | | |
| chest sounds | | | | | |
| ●endotracheal tube | | | | | |
| ●Demerol | | | 50 | | |
| ●Aminophylline | | | | | |
| ●Amoxicillin | | | | | |
| medication infusions PLACEHOLDER | | | | | | respiratory
medication patient name
flowsheet name: general
patient I.D.
flowsheet

| | 01/25 23:00 | 01/26 00:00 | 01/26 01:00 | 01/26 02:00 | 01/26 03:00 |
|---|---|---|---|---|---|
| cough | | productive | | | |
| chest sounds | | | | | |
| endotracheal tube | | | | | |
| Demerol | | | | | |
| Aminophylline | | | | | |
| Amoxicillin | | | | | |
| medication infusions PLACEHOLDER | | | | | |

| | 01/25 23:00 | 01/26 00:00 | 01/26 01:00 | 01/26 02:00 | 01/26 03:00 |
|---|---|---|---|---|---|
| cough | none | productive | | | |
| sputum color | | | | | |
| sputum amount | | | | | |
| chest sounds | | | | | |
| • endotracheal tube | | | | | |
| • Demerol | | | | | |
| • Aminophylline | | | | | |
| • Amoxicillin | | | | | |
| medication infusions PLACEHOLDER | | | | | | respiratory
medication flowsheet
patient name — 1301
patient I.D. — 1302
flowsheet name — 1303: general
1311 cough
1314 sputum color
1315 sputum amount
1312 chest sounds
1315 endotracheal tube — 1310
1321 Demerol
1322 Aminophylline
1323 Amoxicillin
1324 medication infusions PLACEHOLDER — 1320
1351, 1352, 1353, 1354, 1355 (column headers)
1361 productive
1300 flowsheet

| | 01/25 23:00 | 01/26 00:00 | 01/26 01:00 | 01/26 02:00 | 01/26 03:00 |
|---|---|---|---|---|---|
| cough | | | | | |
| chest sounds | | | | | |
| • endotracheal tube | | | | | |
| • Demerol | | | | | |
| • Aminophylline | | | | | |
| • Amoxicillin | | | | | |
| • Dopamine infusion | | | | | | patient Name — 1701
flowsheet name: general — 1703
patient I.D. — 1702
flowsheet — 1700 respiratory — 1710 (1711 cough, 1712 chest sounds, 1713 endotracheal tube)
medication — 1720 (1721 Demerol, 1722 Aminophylline, 1723 Amoxicillin, 1725 Dopamine infusion)

Times: 1751, 1752, 1753, 1754, 1755

| | 01/25 23:00 | 01/26 00:00 | 01/26 01:00 | 01/26 02:00 | 01/26 03:00 |
|---|---|---|---|---|---|
| cough | | | | | |
| chest sounds | | | | | |
| endotracheal tube | | | | | |
| respiratory notes | | | shale | | |
| • Demerol | | | | | |
| • Aminophylline | | | | | |
| • Amoxicillin | | | | | |
| medication infusions PLACEHOLDER | | | | | |

METHOD AND SYSTEM FOR FLEXIBLY ORGANIZING, RECORDING, AND DISPLAYING MEDICAL PATIENT CARE INFORMATION USING FIELDS IN A FLOWSHEET

TECHNICAL FIELD

The invention relates generally to a the field of patient information management, and, more specifically, to the field of medical patient care information organization and display.

BACKGROUND OF THE INVENTION

The provision of health care services to patients depends on the maintenance of significant quantities of patient information, including both clinical information relating to patient treatment and patient management information, such as referral, admission, insurance, and billing information. Health care providers have traditionally maintained such patient information manually, on physical "charts" comprised of paper forms, also known as "flowsheets." Such flowsheets typically show a time series progression of different pieces of patient information. Such pieces of patient information are commonly called "parameters," and may include information about indications of patient condition, laboratory test results, assessments, and the administration of treatments. Parameters may also include administrative information, such as details relating to facility, supply, and human resource usage.

The maintenance of patient information in physical charts often has significant disadvantages. Physical charts may only be viewed or modified in a single physical location. Also, data collected automatically from medical sensors and medical laboratories may not be automatically posted to physical charts. Physical charts further are subject to inadvertent destruction, and may contain illegible information. Disadvantages such as the above militate toward automating the maintenance of patient information.

Existing alternatives for automating the maintenance of patient information fall into the categories of general-purpose databases and rigid patient information databases, both of which have significant disadvantages. General-purpose databases generally lack any measure of support for the medical environment, as they generally do not include tools for entering and viewing information in familiar flowsheet formats and do not provide any basis for organizing patient information in a manner useful to health care providers. Rigid patient information databases, on the other hand, define a particular organization of particular parameters. Neither the parameter organization nor the parameters themselves are typically modifiable by the health care provider. It can be difficult for a health care provider to adapt to a rigid organization of patient information. More seriously, a health care provider that deems the tracking of a particular parameters not specified by the rigid patient information database to be necessary to responsible patient care may be precluded from recording these parameters, or may at least be forced to record these parameters manually. The above-discussed drawbacks of general-purpose databases and rigid patient information databases demonstrate a need for a method and system for flexibly organizing, recording, and displaying medical patient care information.

SUMMARY OF THE INVENTION

The present invention provides a method and system for flexibly organizing, recording, and displaying medical patient care information. In a preferred embodiment, a patient information management facility enables users to customize a patient information hierarchy, which defines and organizes the information that may be stored about each patient, as well as patient data flowsheets, which define views in which the patient data stored according to the hierarchy may be entered and viewed, in a way that is optimized for the structure and procedures of the particular health care organization. The facility enables users to add, modify, and rearrange global or local patient information parameters that make up the hierarchy. Users may define the parameters to be any of a number of types. The user may also customize flowsheets used for entering and displaying result values of parameters defined in the hierarchy for particular patients. The user may expand and contract overview encapsulating parameters to display or hide the encapsulated parameters encapsulated therein. The facility also allows the user to link a result value of one parameter to other parameters, causing the linked-to parameters to be displayed when the result value is entered.

BRIEF DESCRIPTION OF THE DRAWINGS

FIG. 4 is a tabular diagram showing the parameter definition table.

FIG. 7 is a diagram showing the contents of a sample result table.

FIG. 8 shows the display of a flowsheet having the sample flowsheet definition.

FIG. 11 is a screen diagram showing the user entering a result value.

FIG. 13 is a display diagram showing the addition of linked-to parameters to the flowsheet in response to the entry of a linked-from result value.

FIG. 14 is a screen diagram showing the addition of a respiration parameter to the sample flowsheet.

FIG. 17 is a display diagram showing the replacement of placeholder 824 with the Ibuprofen parameter 925.

FIG. 20 is a screen diagram showing a parameter of the note data type displayed in abbreviated form.

DETAILED DESCRIPTION OF THE INVENTION

A method and system for flexibly organizing, recording, and displaying medical patient care information is provided. In a preferred embodiment, health care organizations are provided with a patient information system. A patient information management facility of the patient information system ("the facility") is comprised of software tools that enable each health care organization to customize the patient information system in a way that is optimized for the structure and procedures of the health care organization. The facility permits users to customize a patient information hierarchy ("the hierarchy"), which defines and organizes the information that may be stored about each patient. The facility further permits users to customize patient data flowsheets ("flowsheets"), which define views in which patient data stored according to the hierarchy may be entered and viewed.

The facility enables authorized users of the patient information system to add to, modify, and rearrange the patient information parameters ("parameters") that make up the hierarchy. If parameters at two different points in the hierarchy have the same name, the parameters may either be global or local. If the parameters are global, they share a single set of result values for each patient. On the other hand, if they are local, the parameters each have their own set of result values for each patient. Users may flexibly define the parameters to be any of a number of types. Many of the parameter types specify a time sequence of values.

The facility further enables users to customize flowsheets that may be used for entering and displaying result values for subsets of the parameters defined in the hierarchy for particular patients. Flowsheets may contain parameters defined in the hierarchy as encapsulating parameters and parameters that are linked to other parameters. When displaying a flowsheet containing an encapsulating parameter that encapsulating one or more other parameters, the facility preferably enables the user to toggle between expanding the encapsulating parameter to display its encapsulated parameters and their result values and contracting the encapsulating parameter to display only the encapsulating parameter name. When displaying a flowsheet containing a parameter defined as a linked-from parameter, if the user enters a result value for the linked-from parameter that is linked to other fields, the facility preferably adds these linked-to parameters to the flowsheet. The flowsheets displayed by the facility may further contain parameter placeholders that the user may replace with particular parameters.

Figure 1:
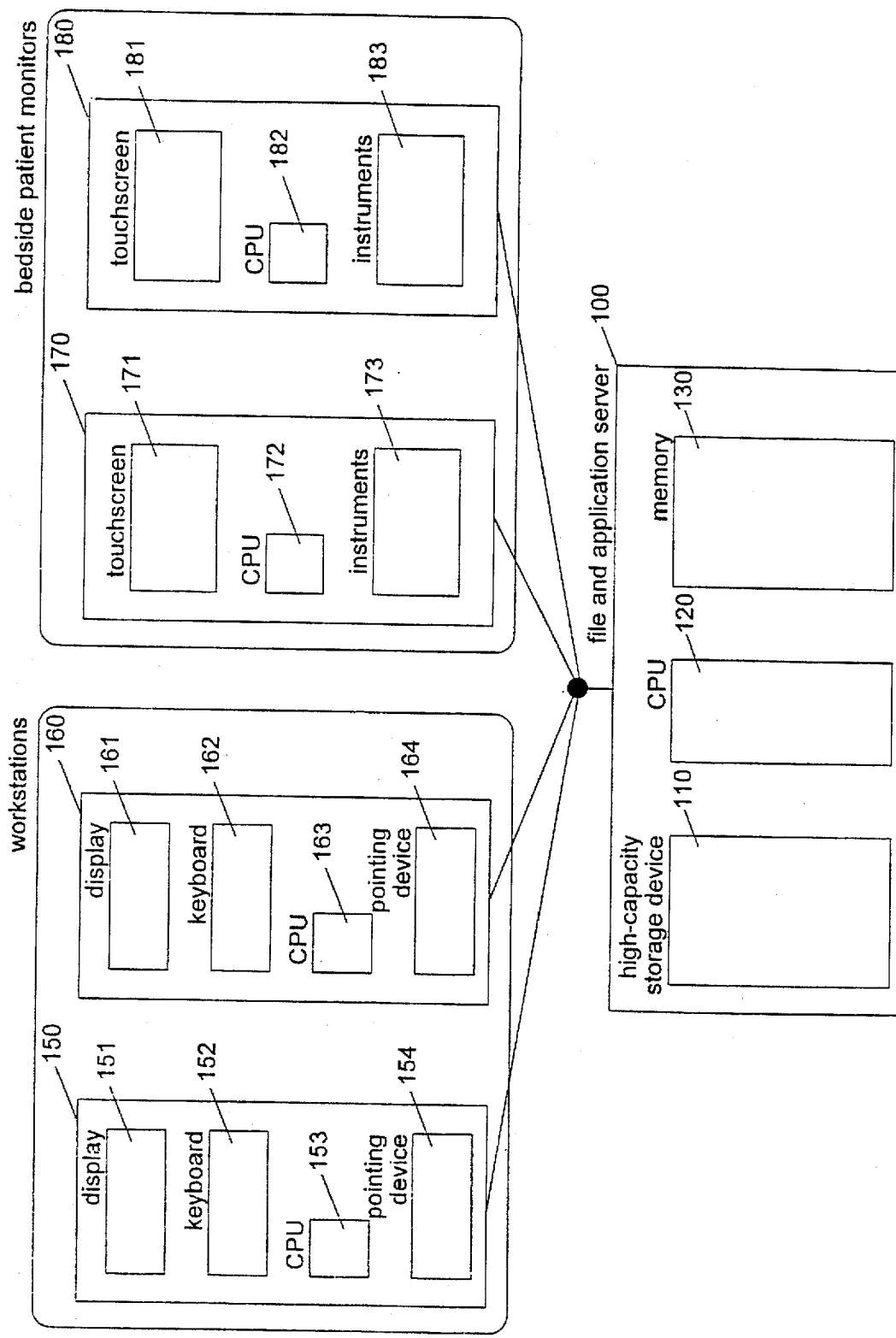
FIG. 1 is a high-level block diagram of the general-purpose computer system upon which the facility preferably operates.

FIG. 1 is a high level block diagram showing the computer network upon which the facility preferably operates. The network connects a file and application server computer system 100 with workstation computer systems, such as 150 and 160, and bedside patient monitor in computer systems, such as 170 and 180. While only a small number of workstation computer systems and bedside patient monitoring computer systems are shown for clarity, it will be recognized by those skilled in the art that a typical network may contain many more of both types of computer systems. The file and application server computer system 100 contains a high-capacity storage device 110, such as a hard disk drive; one or more central processing units (CPUs) 120; and random access memory 130. The patient information system is maintained on the file and application server 100. Workstation computer systems, such as 150, contain a display device 151 such as a video monitor, a keyboard 152; one or more CPUs 153; and a pointing device 154 such as a mouse. The workstation computer systems 150, 160 may be used to access the patient information system. Bedside patient monitoring computer systems, such as 170, are used for collecting data from electronic medical instruments 173 and displaying it on a touch screen 171. The bedside patient monitoring computer systems 170, 180 also have one or more CPUs 172, and may be used to access the patient information system. While the preferred embodiment is shown in FIG. 1, those skilled in the art will appreciate that the facility may operate on virtually any network configuration.

Figure 2:
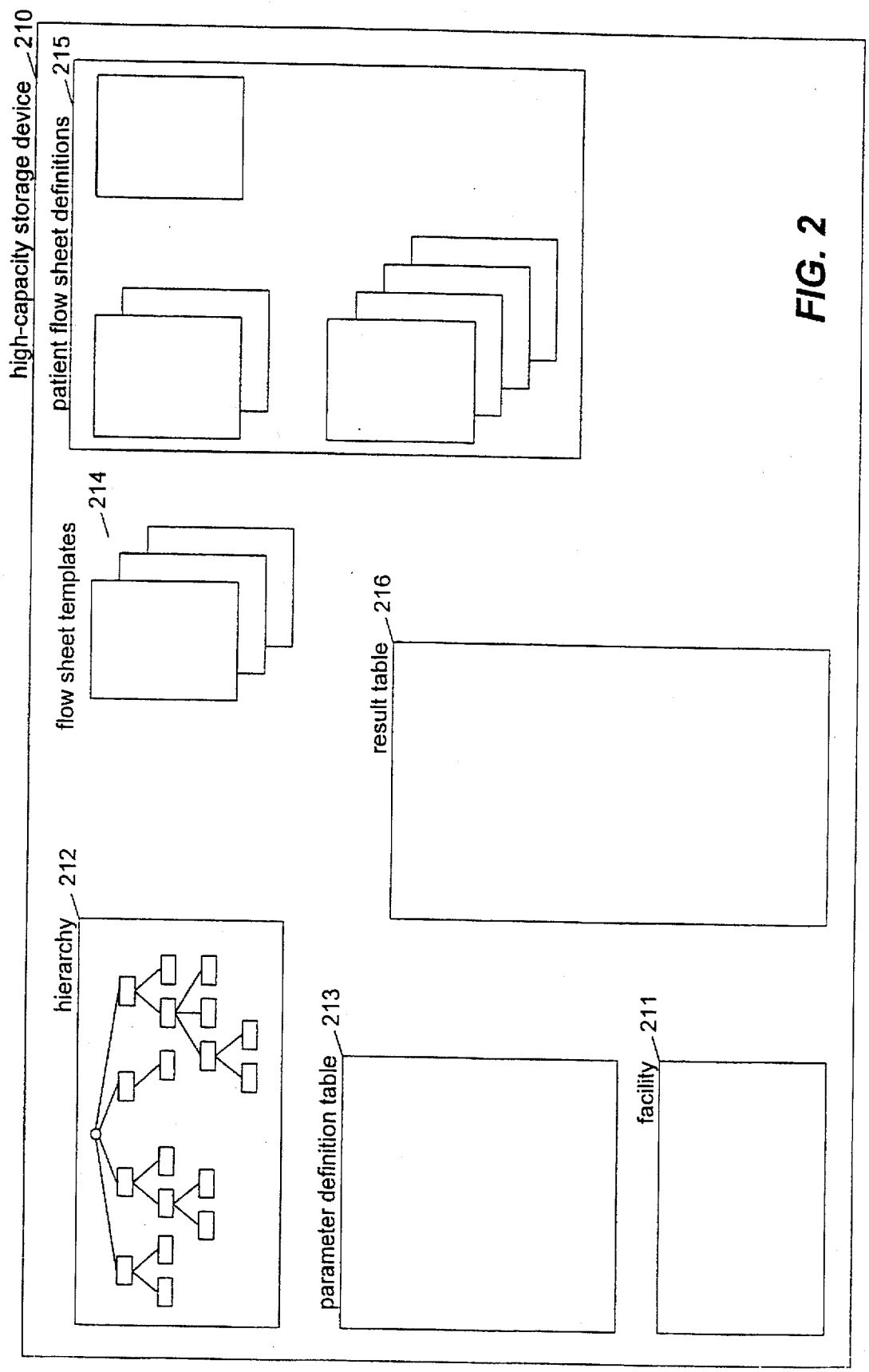
FIG. 2 is a block diagram showing the contents of the high-capacity storage device of the file and application server computer system.

FIG. 2 is a block diagram showing the contents of the high-capacity storage device 110 of the file and application server computer system 100. The high-capacity storage device 110 contains a facility 211 that enables users to interact with the patient information system. The facility is discussed in greater detail below. The high-capacity storage device contains a patient information hierarchy 212. The patient information hierarchy is used to organize the parameters, in conjunction with which pieces of patient information are stored, in a logical organization from which users may easily select them. Authorized users may modify the hierarchy by adding or deleting parameters, or by relocating parameters within the hierarchy. The patient information hierarchy is discussed in greater detail below in conjunction with FIG. 3. The high-capacity storage device also contains a parameter definition table 213. The parameter definition table contains definitional information for each parameter identified in the patient information hierarchy 212, and is discussed below in greater detail in conjunction with FIG. 4. The high-capacity storage device also contains flowsheet definition templates 214. Authorized users may modify existing flowsheet definition templates and add new flowsheet definition templates. The flowsheet definition templates each define a patient-independent flowsheet for entering and viewing parameters in their result values. Any of the flowsheet definition templates may be used for any patient. The high-capacity storage device further contains patient flowsheet definitions 215. The patient flowsheet definitions are used for particular patients to enter and display parameters and their result values. The patient flowsheet definitions may either be automatically copied ("templated") from the flowsheet definition templates 214, or may be created from scratch. Users may modify patient flowsheet definitions. The high-capacity storage device further contains a result table 216. The result table stores all of the parameter result values corrected for each station. The result table is discussed in greater detail below in conjunction with FIG. 7.

Figure 3:
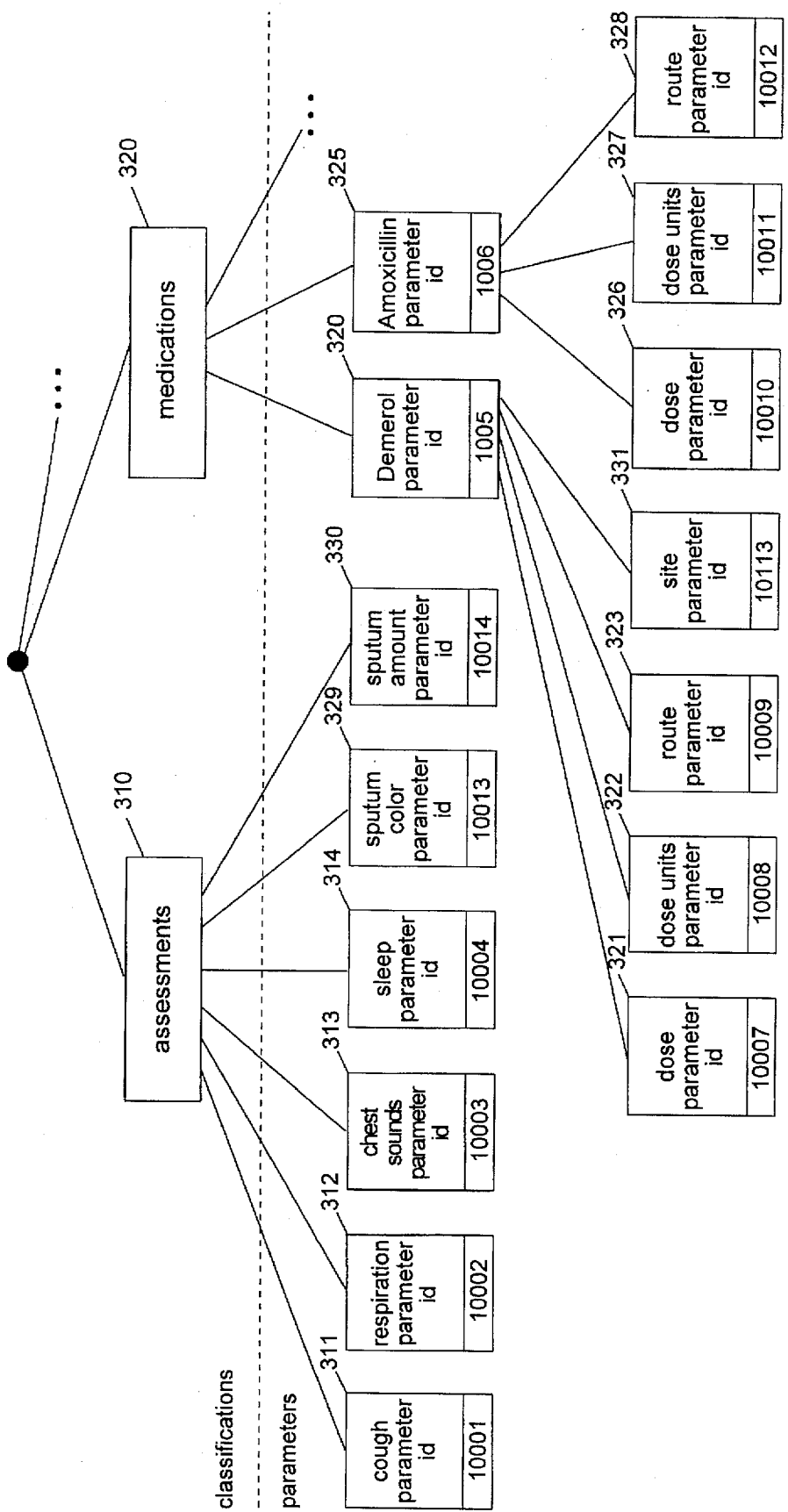
FIG. 3 is a diagram showing the patient information hierarchy.

FIG. 3 is a diagram showing the patient information hierarchy, which is comprised of classifications, such as 310 and 320, and parameters, such as 311–331. The classifications correspond to different categories of parameters, under which parameters may be grouped in a way that is logical to users of the patient information system. For example, the assessments classification 310 contains parameters relating to observable aspects of patient condition, while the medications 320 contains parameters relating to the administration of particular medications. The parameters correspond to actual pieces of patient data that may be stored and displayed for each patient. For example, the cough parameter 311 corresponds to a parameter that indicates whether a particular patient at a particular time exhibits no cough, a nonproductive cough, or a productive cough. Each of the parameters contains a parameter identifier ("parameter i.d."). The labels shown in conjunction with each parameter, such as "cough parameter i.d." shown in conjunction with cough parameter 311, are for illustrative purposes only and not actually stored in the tree comprising the patient information hierarchy. Each of the parameters that constitutes a leaf of the tree, e.g., 311–314, 321–323, 326–328, and 329–331, is called a result parameter, and may contain a result value for a particular patient at a particular time. Parameters that are not leaves of the tree, e.g., 320 and 325, are called encapsulating parameters. Encapsulating parameters may not contain result values, but rather "encapsulate," or represent at a high level, one or more other parameters, called "encapsulated parameters." For example, encapsulating parameter 320 (Demerol) encapsulates encapsulated parameters 321, 322, 323, and 331 (dose, dose units, route, and site).

FIG. 4 is a tabular diagram showing the parameter definition table. The parameter definition table contains definitional information for each parameter identified in the patient information hierarchy. The parameter definition table 400 contains the following columns, or fields, which may each contain information for each parameter: parameter i.d. column 401, parameter name 402, linked-from parameter column 403 which contains an indication of whether the parameter is linked to any other parameters, a parameter data type 404, a normal value 405 containing a result value for the parameter that a well patient, and a column containing data type-specific information 406. Table 1 below shows the nature of data type-specific information for several data types.

TABLE 1

| parameter data type | data type-specific information |
| --- | --- |
| selection | choices, linked parameters i.d.s therefor and primary encapsulated parameter |
| encapsulating | parameter i.d.s of encapsulated parameters |
| calculated | formula |
| string | (none) |
| integer | (none) |
| note | (none) |
| float | (none) |

The rows are preferably indexed on the parameter i.d. column to allow the row for a particular parameter to be quickly retrieved using the parameter i.d. of the parameter. Each row of the table corresponds to a single parameter identified in the patient information hierarchy. For example, the row for parameter i.d. 10001 shows the name of the parameter to be cough, the parameter to be a linked-from parameter, the parameter to be of the select data type, the normal value of the parameter to be none and the selection choices stored in the data-type-specific information column to be none, non-productive, and productive. The data-type-specific information column further indicates that the productive selection choice is linked to the parameters having parameter i.d.s 10013 and 10014. The row for parameter i.d. 1005 shows that the Demerol parameter is of the encapsulating data type, that it encapsulates the parameters having parameter i.d.s 10007, 10008, and 10009, and that the parameter having parameter i.d. 10007 is its primary encapsulated parameter.

Figure 5:
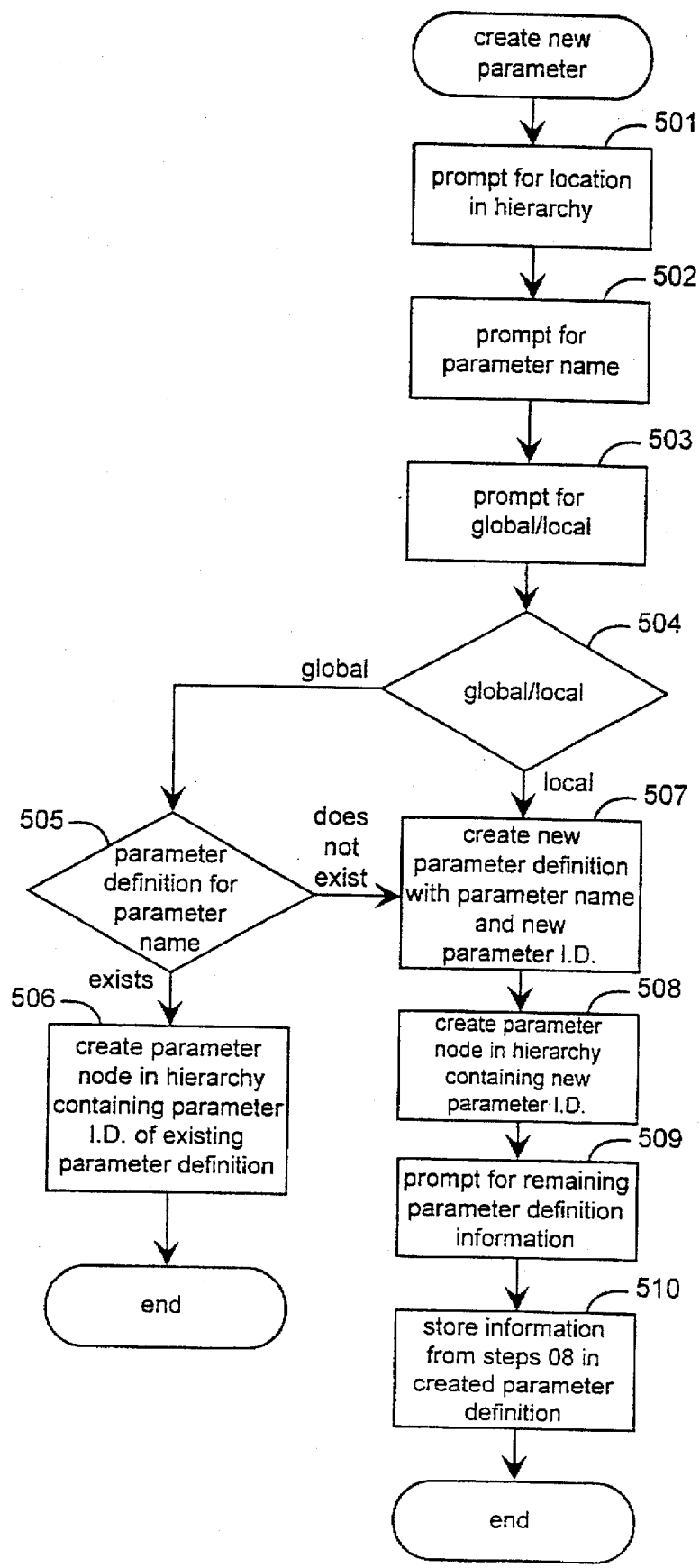
FIG. 5 is a flow diagram showing the steps performed by the facility in order to create a new parameter.

Authorized users may create new parameters in order to store and display new pieces of patient information, or to represent an existing piece of patient information at an additional location in the hierarchy. FIG. 5 is a flow diagram showing the steps performed by the facility in order to create a new parameter. In step 501, the facility prompts the user for the location of the parameter in the hierarchy. Step 501 preferably involves presenting the user with a list of classifications and receiving input from the user selecting one of the classifications. Step 501 further preferably involves displaying a list of the encapsulating parameters for the selected classification and receiving from the user an indication of which of the encapsulating parameters, if any, the new parameter should be an encapsulated parameter of. In step 502, the facility prompts the user for the name of the new parameter and receives the name of the new parameter from the user. In step 503, the facility prompts the user for an indication of whether the new parameter is global or local. An indication that the new parameter is local indicates that a new row in the parameter definition table should be created for the new parameter, and that a new, unique parameter i.d. should be assigned to the new parameter. A global indication indicates that the facility should search for an existing parameter in the parameter definition table having the same parameter name, and assign the parameter i.d. of the existing parameter to the new parameter. In step 504, if the user indicates that the new parameter is global, then the facility continues at step 505, else if the user indicates that the new parameter should be local, then the facility continues at step 507. In step 505, if a parameter definition for the parameter name selected by the user exists, then the facility continues at step 506, else the facility continues at step 507. In step 506, the facility creates a parameter node in the hierarchy containing the parameter i.d. of the existing parameter definition for the selected parameter name. After step 506, these steps conclude.

In step 507, the facility creates a new parameter definition in the parameter definition table having the selected parameter name and a new, unique parameter i.d. In step 508, the facility creates a parameter node in the hierarchy containing the new parameter i.d. In step 509, the facility prompts the user for the remaining parameter definition information, including parameter data type, normal value, and data type-specific information. The facility preferably uses the data type to determine which data type-specific information to prompt the user for. For example, for a parameter having the encapsulating data type, the facility preferably prompts the user to identify encapsulated parameters, and to indicate which of the encapsulated parameters is the primary encapsulated parameter that is to be displayed in conjunction with the encapsulating parameter when the encapsulating parameter is collapsed. The facility preferably prompts the user for encapsulated parameters by prompting the user to choose them from a list of parameters organized according to the hierarchy. As is discussed in further detail below, to do so, the facility preferably displays a list of default encapsulated parameters associated with the new parameter's classification as encapsulated parameters of the encapsulating parameter, which may each either be retained or deleted by the user. For parameters of the select data type, the facility preferably prompts the user for the selection choices for parameters of the select data type. The facility further preferably prompts the user for any linked-to parameters for each of the selection choices. For parameters of the calculated type, the facility preferably prompts the user for a formula from which result values for the parameter may be calculated. The facility preferably allows the user to enter such a formula using a special visual interface discussed in detail in U.S. application Ser. No. 08/504,703 which is filed concurrently herewith and is hereby incorporated by reference. In step 510, the facility stores the information received in step 509 and the parameter definition created in step 507. These steps then conclude.

Figure 6:
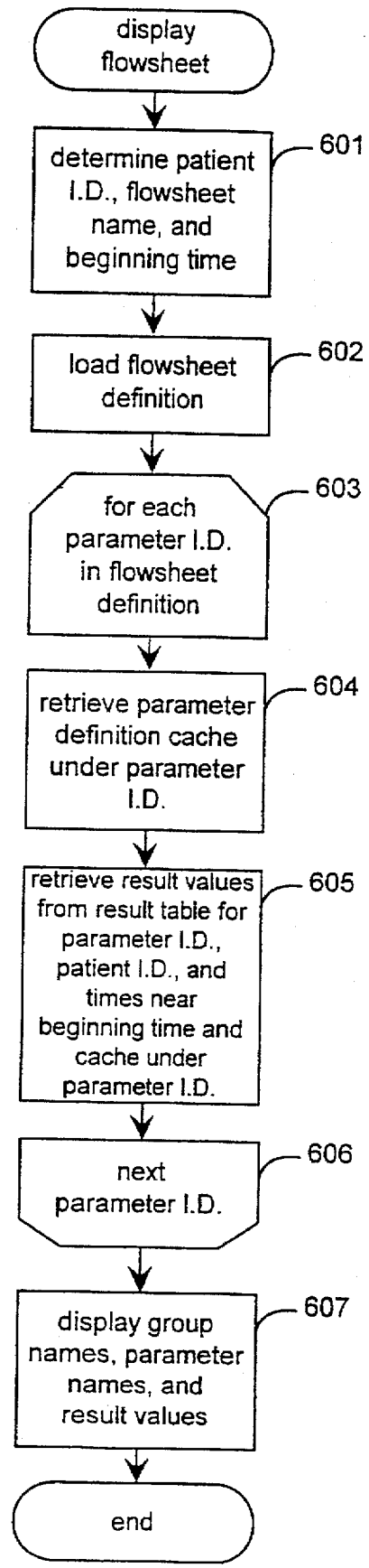
FIG. 6 is a flow diagram showing the steps preferably performed by the facility in order to display a flowsheet for a particular patient.

A user may use a flowsheet to display a set of parameters and their result values for a particular patient over a time. FIG. 6 is a flow diagram showing the steps preferably performed by the facility in order to display a flowsheet for a particular patient. In step 601, the facility determines the name of the flowsheet to display, the patient i.d. of the patient for which the flowsheet is to be displayed, and a beginning time at which to begin displaying result values. The user may select either the name of an existing patient flowsheet definition 215, or the name of a flowsheet definition template 214. If a patient flowsheet definition having the selected name exists for the selected patient i.d., the facility loads this patient flowsheet definition in step 602. If no patient flowsheet definition exists for this flowsheet name, the facility preferably copies the flowsheet definition template having this flowsheet name to create a patient flowsheet definition having this name and the patient i.d. of the selected patient in step 602. The facility then loads this new patient flowsheet definition in step 602. Table 2 below shows a sample flowsheet definition.

TABLE 2

Sample flowsheet definition

| | | |
|---|---|---|
| 1 | group respiratory | |
| 2 | { | <cough parameter i.d.> 10001 |
| 3 | | <chest sounds parameter i.d.> 10103 |
| 4 | | <endotracheal tube parameter i.d.> 10204 |
| 5 | } | |
| 6 | | |
| 7 | group medications | |
| 8 | { | <Demerol parameter i.d.> 10005 |
| 9 | | <Aminophylline parameter i.d.> 10037 |
| 10 | | <Amoxicillin parameter i.d.> 10006 |
| 11 | | <medication infusions placeholder> 90005 |
| 12 | } | |

The sample flowsheet definition is comprised of definitions for two flowsheet groups. A flowsheet group is a collection of parameters that are related for purposes of displaying result values for and adding result values to parameters in the flowsheet. The parameters contained in a particular flowsheet group may be selected from any point in the hierarchy, including points in the hierarchy under different classifications. A respiratory group is defined in lines 1–5, and a medications group is defined in lines 7–12. Each of lines 2–4 identify a parameter in the respiratory group. For example, line 2 identifies the cough parameter of the assessments classification, and contains the parameter i.d. for the cough parameter, 10001. The label text, e.g., "<cough parameter i.d. >", is merely illustrative, and is not actually included in the flowsheet definition. The sample flowsheet definition further contains a parameter placeholder on line 11, which allows users to easily add a particular parameter to the flowsheet during flowsheet use. Lines 3 and 4 identify a chest sounds parameter of the respiratory assessments classification and an endotracheal tube parameter of the tubes classification. The sample flowsheet definition causes the facility to display a flowsheet containing a respiratory group and a medications group. Each parameter identified with each group is displayed in conjunction with its result values for the relevant period of time. FIG. 8 shows the display of a flowsheet having the sample flowsheet definition, and is discussed in greater detail below.

In steps 602–606, the facility loops through each parameter i.d. contained in the flowsheet definition. Steps 604–605 are therefore repeated for each parameter i.d. In step 604, the facility retrieves the parameter definition for the parameter i.d. from the parameter definition table 400 and caches it in memory, indexed by the parameter i.d. In step 605, the facility retrieves the result values from the result table 700 having the parameter i.d., the current patient i.d., and a time near the beginning time. The facility further caches the retrieved result values in memory, indexed by the parameter i.d.

FIG. 7 is a diagram showing the contents of a sample result table. The sample result table contains patient i.d. column 701, parameter i.d. column 702, result time column 703, and result value column 704. The table is preferably indexed by the patient i.d., parameter i.d., and result time columns to facilitate rapid retrieval of its rows. Each row of the result table, e.g., 711–718, contains a single result value for a particular parameter at a particular time for a particular patient. For example, row 712 indicates that the patient having patient i.d. 100001 for the respiration parameter having parameter i.d. 100003 at 11:00 p.m. on Jan. 25th had a result value of high. While the contents of the result time and the result value column may be encoded to minimize the storage resources consumed by the result table, the contents of these columns are preferably stored in full textual form in order to ensure that backups of the result table will be restorable. After each parameter i.d. in the flowsheet definition has been processed, the facility continues at step 607. In step 607, the facility displays the group names in the flowsheet definition, and, for each parameter i.d. in the flowsheet definition, the parameter name and result values. These steps then conclude.

FIG. 8 is a screen diagram showing the display of the sample flowsheet 800. The flowsheet displays the name of the patient 801 and the corresponding patient i.d. 802 to identify the patient for which result values are displayed. The flowsheet also displays the name of the flowsheet 803. Along the left, the flowsheet displays the names of the parameters in each of the groups identified in the flowsheet definition. For example, the respiratory group 810 is displayed, which contains the cough parameter 811, the chest sounds parameter 812, and the endotracheal parameter 813. The medications group 820 similarly contains parameters 821–823. To the right of each parameter is a series of cells in which to display result values for that parameter for the designated patient times near the beginning time. Above the cells are time labels 851–855. Each time label represents a point in time for which parameters may have a result value. For example, cell 891 shows that the cough parameter 811 has a result value of none for time 851, i.e., 11:00 p.m. on Jan. 25th.

In FIG. 8, the facility has displayed round bullets in from of parameter names for parameters 821–823, indicating that they are encapsulating parameters rather than result parameters and that they do not directly contain any result values. As discussed above, encapsulating parameters may either be displayed in collapsed form, in which only the encapsulating parameter is displayed (as shown in FIG. 8), or in an expanded form, in which the encapsulated parameters encapsulated by the encapsulating parameter are displayed beneath the encapsulating parameter.

Figure 9:
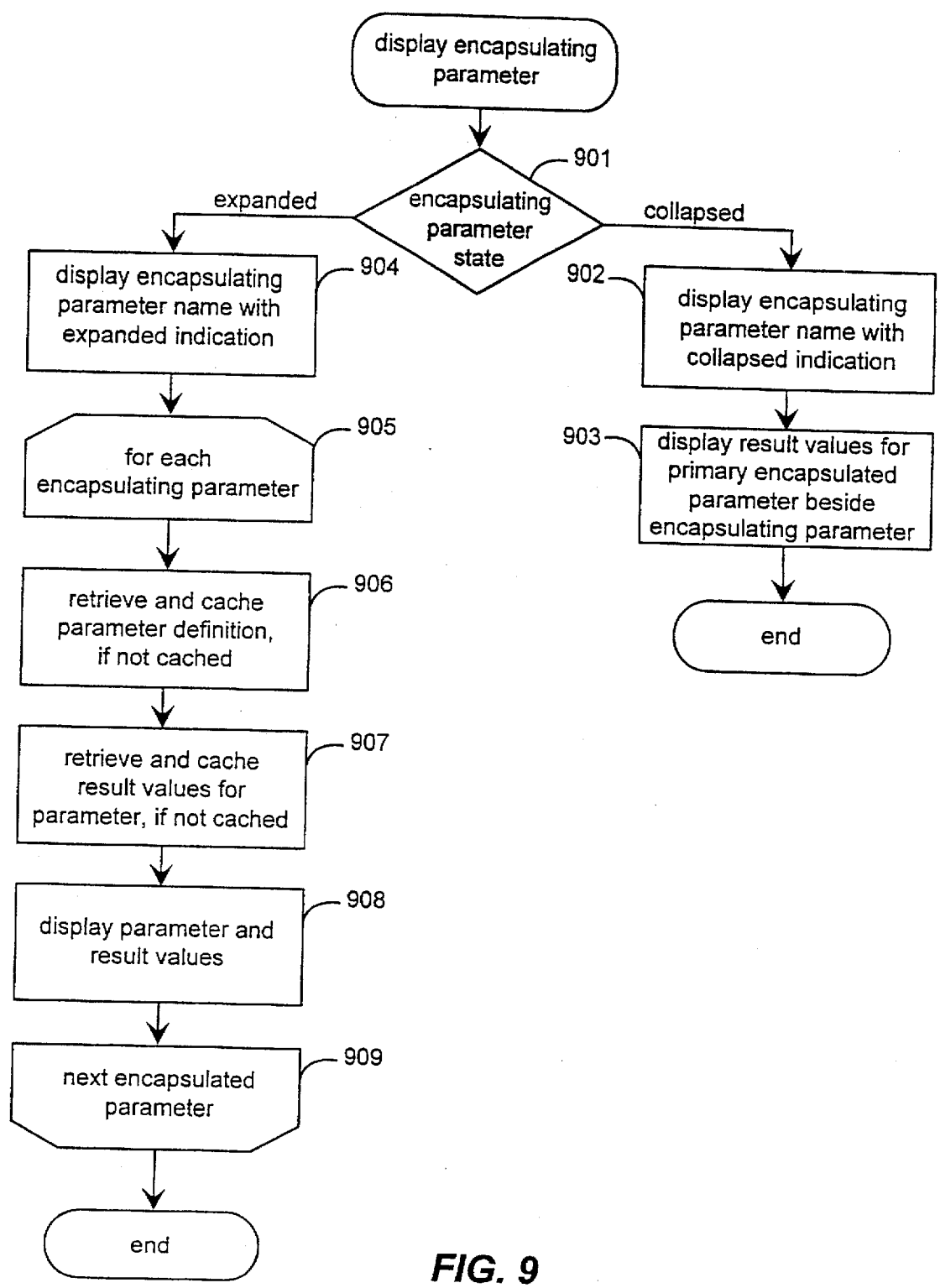
FIG. 9 is a flow diagram showing the steps preferably performed by the facility in order to display each encapsulating parameter.

FIG. 9 is a flow diagram showing the steps preferably performed by the facility in order to display each encapsulating parameter. The collapsed/expanded state of the encapsulating parameter may be toggled by the user by clicking on the expanded or collapsed indication with which the encapsulating parameter name is displayed. In step 901, if the encapsulating parameter is collapsed, then the facility continues at step 902, else if the encapsulating parameter expanded, then the facility continues at step 904. In step 902, the facility displays the name of the encapsulating parameter with a round bullet to indicate that the encapsulating parameter is collapsed. In step 903, if a primary encapsulated parameter is defined in the parameter definition for the encapsulating parameter, the facility displays result values for the primary encapsulated parameter beside the encapsulating parameter. An example is result value 892, which is a result value for the dose encapsulated parameter of the Demerol encapsulating parameter that is displayed beside the Demerol encapsulating parameter. After step 903, these steps conclude.

Figure 10:
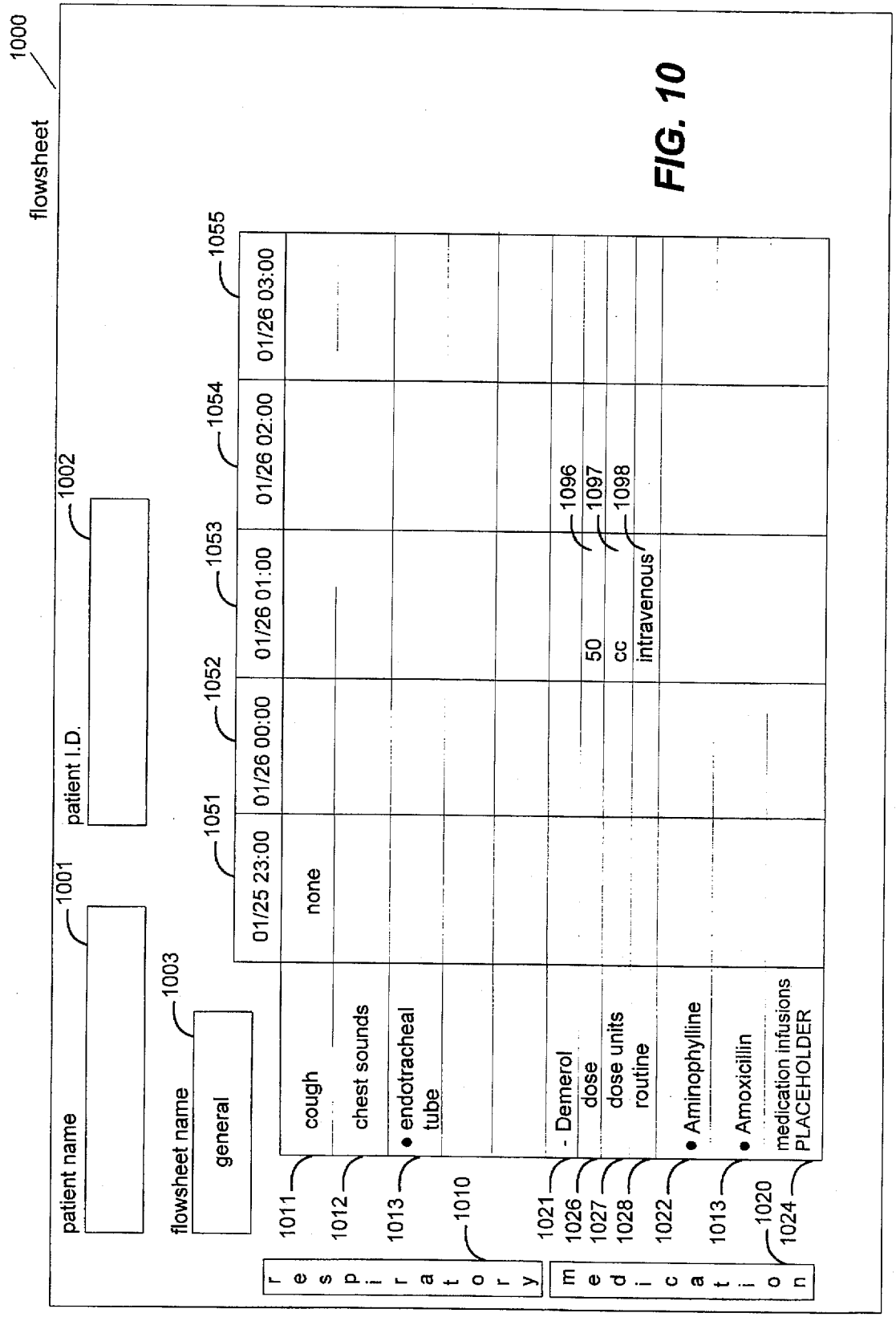
FIG. 10 is a screen diagram of the sample flowsheet in which an encapsulating parameter has been expanded.

In step 904, the facility displays the encapsulating parameter name with an expanded indication. FIG. 10 is a screen diagram of the sample flowsheet in which the Demerol parameter 1021 has been expanded. The diagram shows that the Demerol parameter 1021 is displayed with a horizontal bar indicating that the encapsulating parameter expanded. In steps 905–909, the facility loops through each encapsulated parameter of the encapsulating parameter. Steps 906–908 are therefore repeated for each encapsulated parameter. In step 906, the facility retrieves and caches the parameter definition for the encapsulated parameter if it is not already cached. In step 907, if the encapsulated parameter has a result value, the facility retrieves and caches result values for the parameter if result values are not already cached. In step 908, the facility displays the encapsulated parameter and any result values. If the encapsulated parameter is itself an encapsulating parameter, it has its own collapsed/expanded state, and the facility preferably repeats the steps of FIG. 9 recursively for the encapsulated parameter. FIG. 10 shows the display of encapsulated parameters 1026–1028, as well as their corresponding result values 1096–1098. After the facility loops through each encapsulated parameter, these steps conclude.

Figure 12:
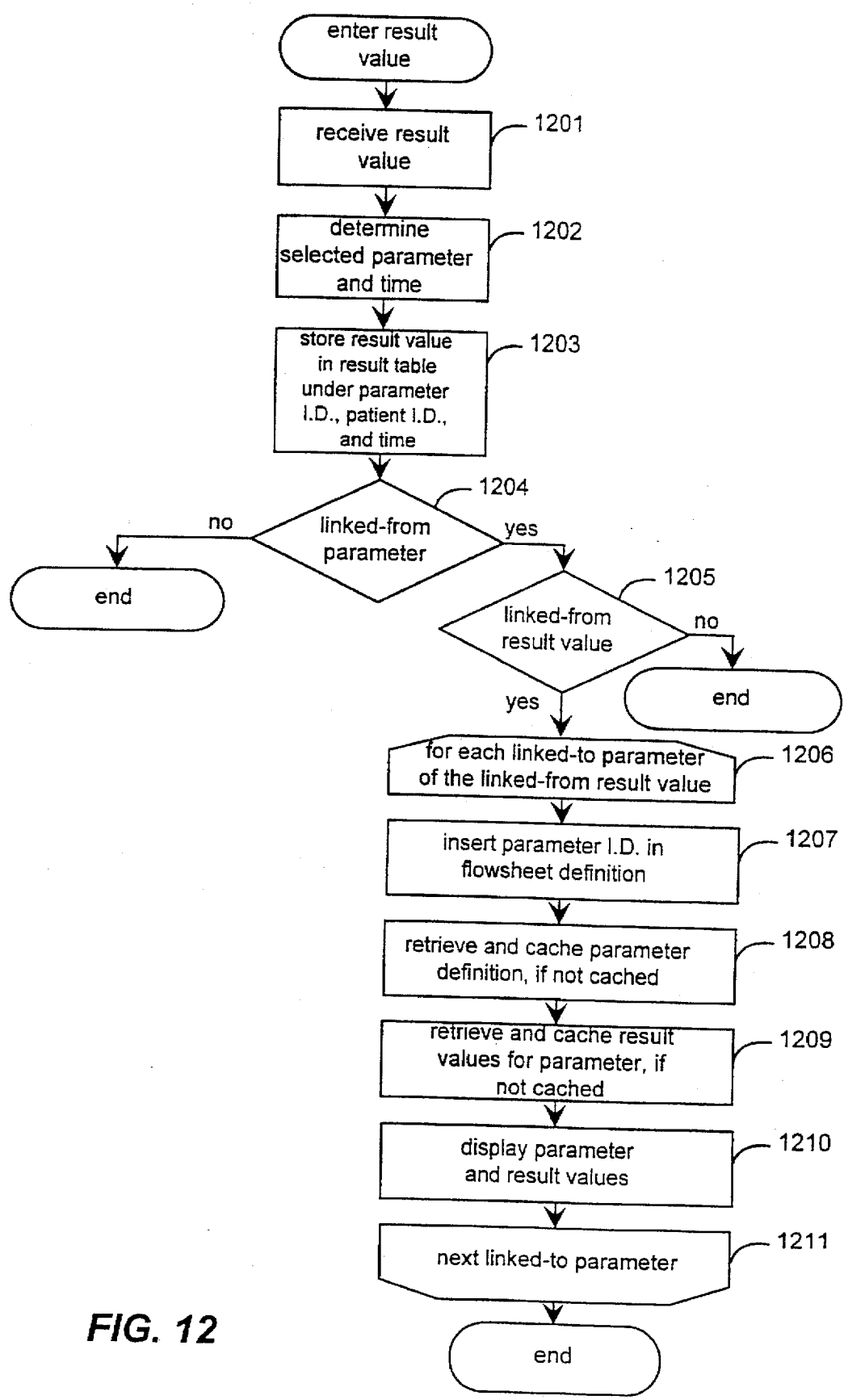
FIG. 12 is a flow diagram showing the steps preferably performed by the facility in order to enter a received result value.

Users may use a flowsheet to enter one or more result values. Result values may also preferably be entered automatically in response to automatically receiving data from electronic medical sensors or from medical laboratories. If the user enters a linked-from result value, the parameters to which the result value are linked are added to the flowsheet. FIG. 12 is a flow diagram showing the steps preferably performed by the facility in order to enter such a received result value. In step 1201, the facility receives the result value. In step 1202, the facility determines the parameter and time for which the result value were received. If the result value is received from a user, step 1202 is performed by determining the parameter and time of the cell that the user selected before entering the result value. FIG. 11 is a screen diagram showing the user entering a result value. The diagram shows the user entering a productive result value 1161 for the cough parameter 1111 at midnight on Jan. 26th. If the result value is received from an external source such as an electronic medical sensor or a medical laboratory, the parameter and time for which the result value was sent is preferably transmitted with the result value. In step 1203, the facility stores the result value by creating a new row in the result table containing the current parameter i.d., patient i.d., and time and the received result value. In step 1204, if the cached parameter definition indicates that the current parameter is a linked-from parameter, then the facility continues at step 1205, else these steps conclude. In step 1205, if the received result value is a linked-from result value for which linked-to parameters are listed in the parameter definition, then the facility continues at step 1206, else these steps conclude. In steps 1206–1211, the facility loops through each linked-to parameter to which the result value is linked. Steps 1207–1210 are therefore repeated for each linked-to parameter. In step 1207, the facility inserts the parameter i.d. for the linked-to parameter in the flowsheet definition after the linked-from parameter. In step 1208, the facility retrieves and caches the parameter definition for the linked-to parameter if it is not already cached. In step 1209, the facility retrieves and caches result values for the linked-to parameter, if not already cached. In step 1210, the facility displays the linked-to parameter and its result values beneath the linked-from parameter. After the facility processes each linked-to parameter, these steps conclude.

FIG. 13 is a display diagram showing the addition of linked-to parameters to the flowsheet in response to the entry of the productive result value 1361 for the linked-from cough parameter 1311. Linked-to parameters sputum color 1314 and sputum amount 1315 have been added to the flowsheet and are displayed under the cough parameter 1311. This permits the user to enter results for these parameters, which often occur in conjunction with the linked-from result value.

Figure 14:
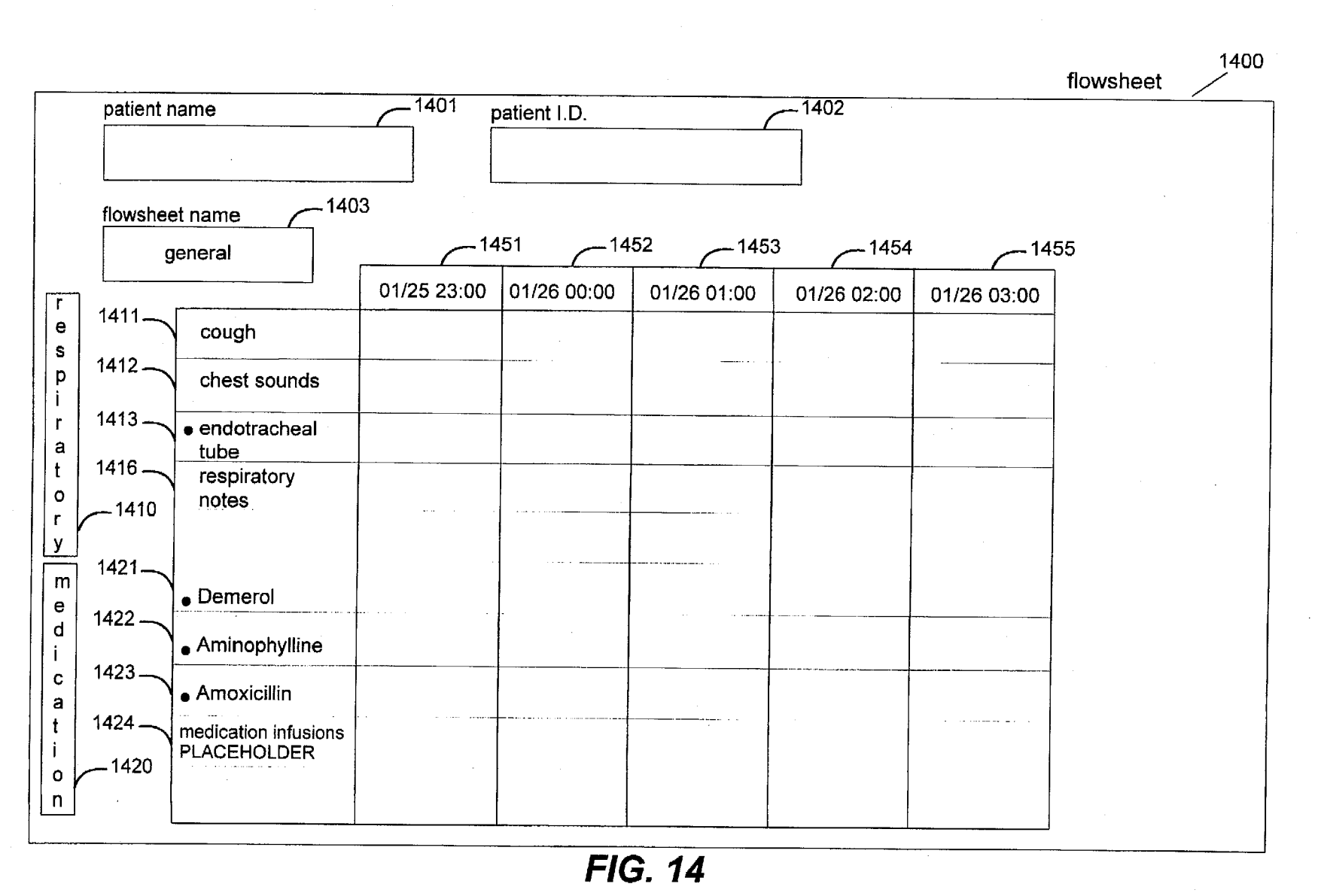
Figure 15:
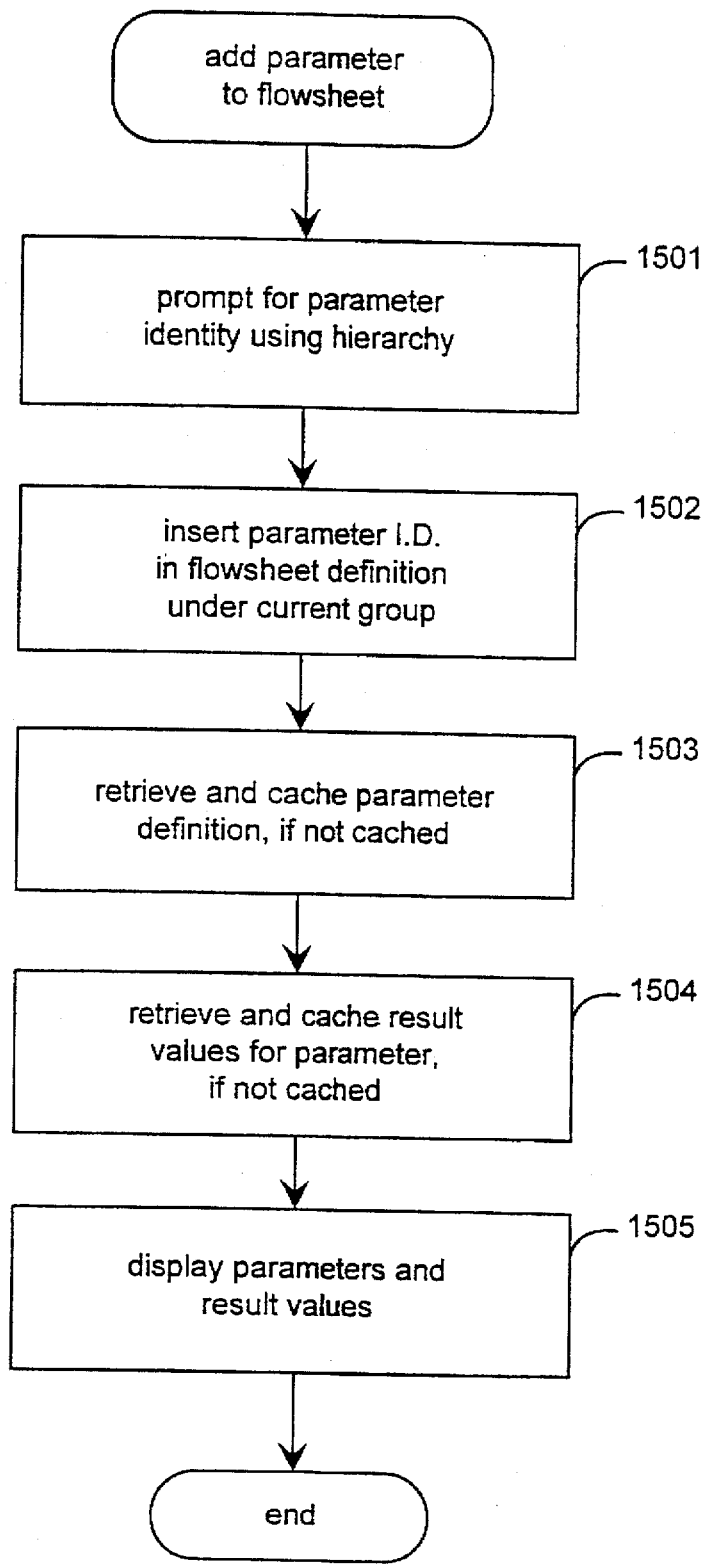
FIG. 15 is a flow diagram showing the steps preferably performed by the facility in order to add a parameter to a flowsheet.

Users may also add a parameter to a flowsheet. A new parameter may be added either to a patient flowsheet or to a flowsheet template. FIG. 14 is a screen diagram showing the addition of a respiratory notes parameter 1416 to the sample flowsheet. FIG. 15 is a flow diagram showing the steps preferably performed by the facility in order to add a parameter to a flowsheet. In step 1501, the facility prompts the user for the identity of the parameter to add to the flowsheet. Step 1501 preferably involves displaying the parameters according to the patient information hierarchy and allowing the user to select one. In step 1502, the facility inserts the parameter i.d. in the flowsheet definition under the current group of the flowsheet. Table 3 shows the addition of line 4A to the sample flowsheet definition, which contains the respiratory notes parameter i.d. 10251.

TABLE 3

| | Sample flowsheet definition |
|---|---|
| 1 | group respiratory |
| 2 | { <cough parameter i.d.> 10001 |
| 3 | <chest sounds parameter i.d.> 10103 |
| 4 | <endotracheal tube parameter i.d.> 10204 |
| 4A | respiratory notes parameter i.d.> 10251 |
| 5 | } |
| 6 | |
| 7 | group medications |
| 8 | { <Demerol parameter i.d.> 10005 |
| 9 | <Aminophylline parameter i.d.> 10037 |
| 10 | <Amoxicillin parameter i.d.> 10006 |
| 11 | <medication infusion placeholder i.d.> 90005 |
| 12 | } |

In step 1503, the facility retrieves and caches the parameter definition for the new parameter if it is not already cached. In step 1504, the facility retrieves and caches result values for the new parameter if they are not already cached. In step 1505, the facility displays the new parameter and its result values. These steps then conclude.

Figure 16:
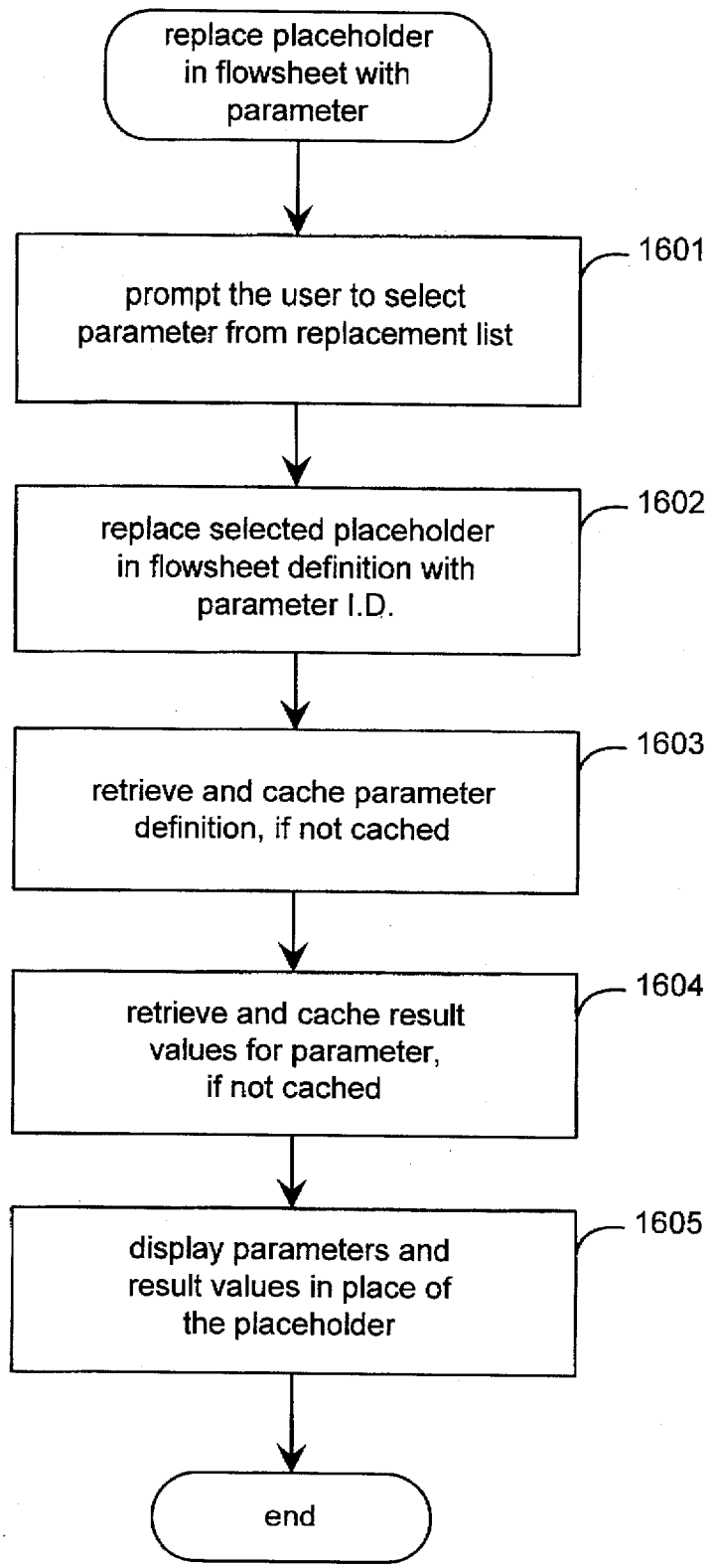
FIG. 16 is a flow diagram showing the steps preferably performed by the facility in order to replace such a placeholder with a particular parameter.

The facility permits parameter placeholders to be included in flowsheet definitions in order to represent a large number of combinations of parameters that are likely to be displayed on the flowsheet. For example, displaying information about a medication infusion can involve the display of many different combinations of parameters. Placeholders are preferably defined in a table analogous to the parameter definition table. Each placeholder has a placeholder i.d., a name, and a list of parameters with which the placeholder may be replaced by the user. When the flowsheet is displayed, a user may select a display placeholder and replace it with one of its replacement parameters. In response, the facility replaces the placeholders with the selected replacement parameter, including any encapsulated parameters encapsulated by the selected replacement parameter. Placeholders, like parameters, may preferably be created and modified by authorized users in order to optimize them for the procedures of a particular health care organization. A placeholder may also encapsulate one or more other parameters or placeholders. Placeholders and parameters encapsulated by a placeholder are handled in the same manner as other placeholders and parameters. FIG. 16 is a flow diagram showing the steps preferably performed by the facility in order to replace such a placeholder with a particular parameter. These steps are largely similar to those shown in FIG. 15 for adding a parameter to the flowsheet, with the following exceptions: step 1601 prompts the user to select the parameter with which to replace the placeholder from the replacement list defined for the placeholder; step 1602 replaces the selected placeholder in the flowsheet definition with the selected parameter i.d.; and step 1605 displays the selected parameter and its results in place of the placeholder. FIG. 17 is a display diagram showing the replacement of medication infusion placeholder 824 with the dopamine infusion parameter 925.

Figure 18:
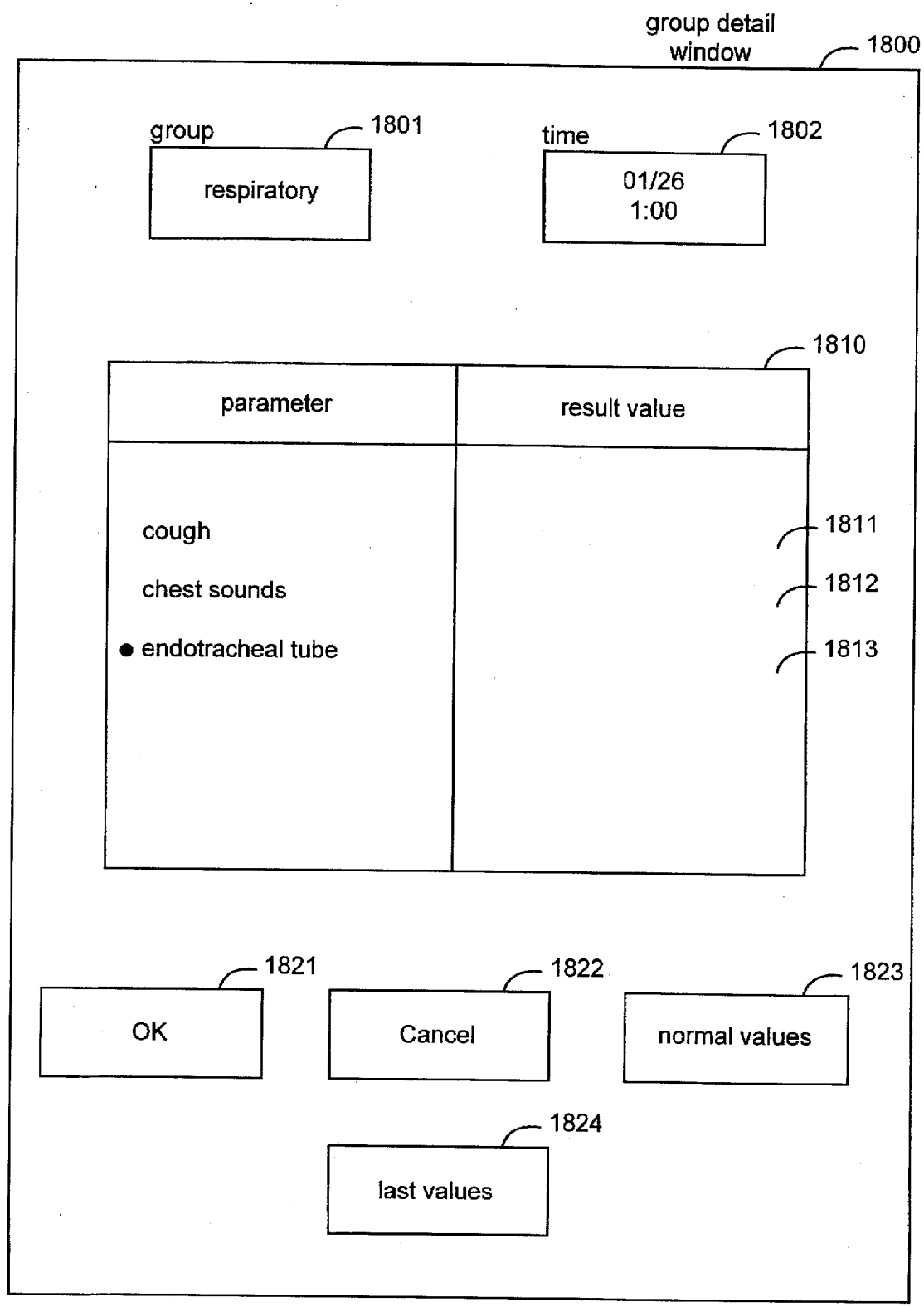
FIG. 18 is a partial screen diagram showing such a group detail window 1800 that contains indications of the selected group 1801 and of the selected time 1802.
Figure 19:
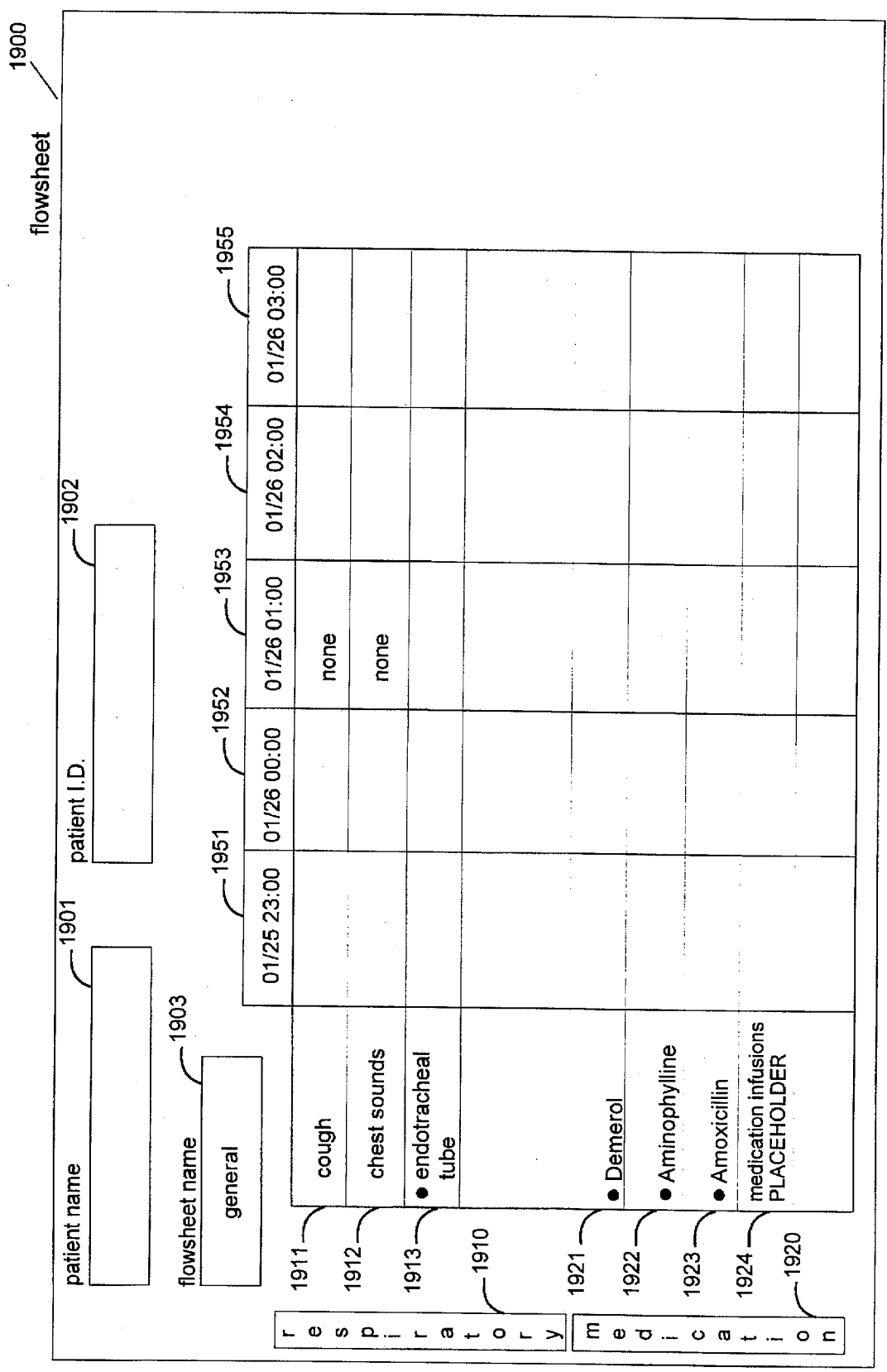
FIG. 19 is a screen diagram showing the entry of the normal values for the respiratory group 1910 at 1:00 A.M. on Jan. 26th.

The facility preferably also enables a user to quickly enter normal result values for each parameter in a group at a particular time. If the user selects a group, such as respiratory group 810 and a time label, such as time label 853 for 1:00 A.M. on Jul. 26th, the facility displays a group detail window. FIG. 18 is a partial screen diagram showing such a group detail window 1800 that contains indications of the selected group 1801 and of the selected time 1802. The window 1800 further contains a table 1810 containing the current result values 1811–1813 for the parameters of the selected group. The window 1800 further contains a normal values button 1823. If the user issues a normal values command by pressing the normal values button, the normal values for each of the parameters in the group are retrieved from their cached parameter definitions and entered as the result values for these parameters at the selected time. FIG. 19 is a screen diagram showing the entry of the normal values for the respiratory group 1910 at 1:00 A.M. on Jan. 26th. For example, the result value for the cough parameter 1911 is none, the normal value for the cough parameter.

Similarly, the facility preferably also enables a user to quickly copy the last result values recorded for each parameter in a flowsheet group forward to a later time. In order to do so, the user presses a last values button 1824 (FIG. 18).

Figure 21:
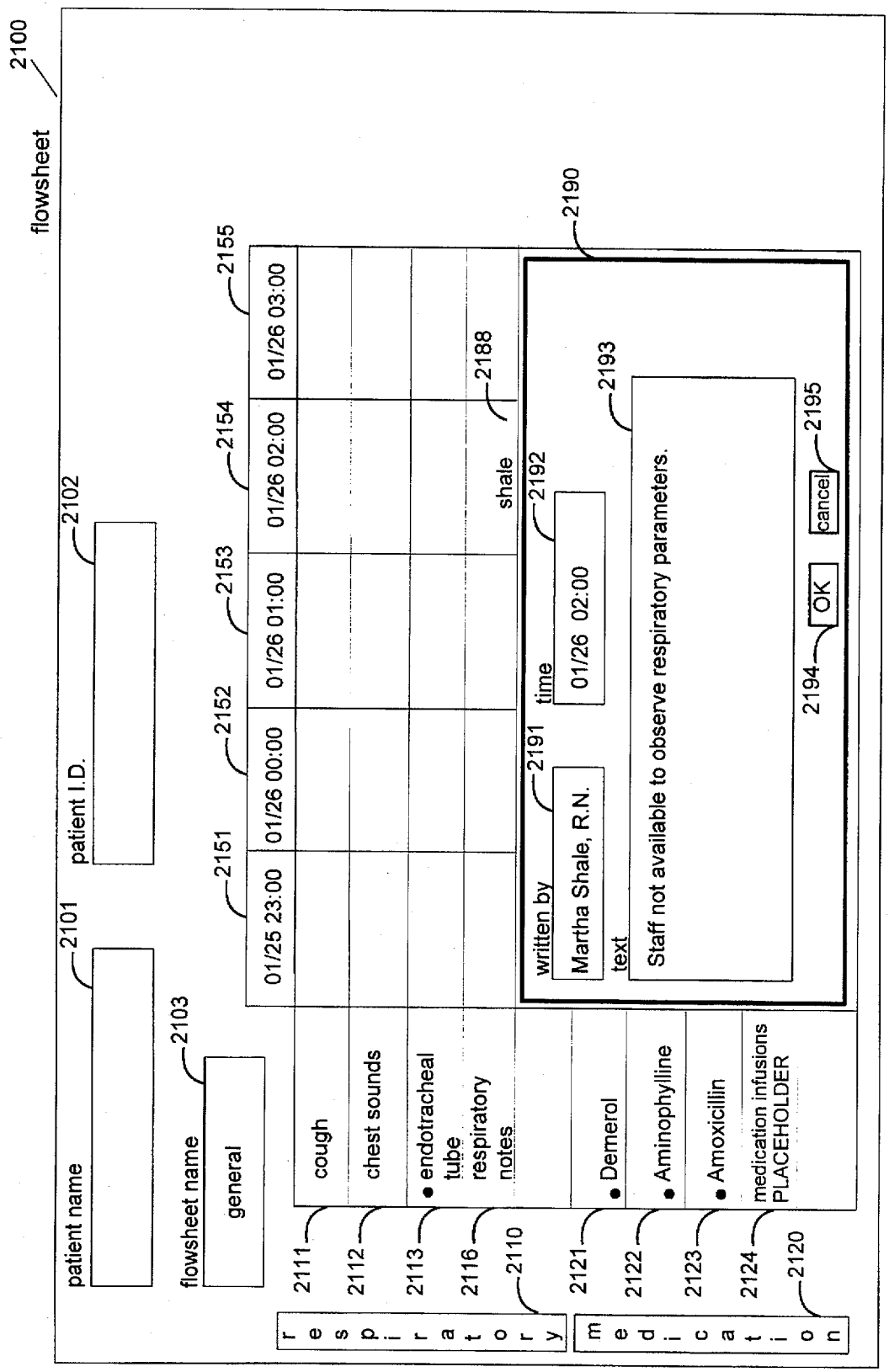
FIG. 21 is a screen diagram showing the display of an entire note parameter result value.

Users may enter result values for parameters of a notes type, which can contain several paragraphs of text. Result values of parameters of the notes type are shown normally shown within a flowsheet in an abbreviated form. FIG. 20 is a screen diagram that showing a note parameter result value 2088 in abbreviated form, which is the last name of the writer. FIG. 21 is a screen diagram showing the display of the entire note parameter result value 2190 when the user selects the cell containing the abbreviated note parameter result value 2188. The entire result value shows all of the information associated with the note, including the full name of the writer 2191, the time at which the note was written 2192, and the complete note text 2193. The user may dismiss the window containing the entire result value by selecting either the OK button 2194 or the cancel button 2195.

The facility further permits users to specify, for each classification, one or more default parameters. When the user creates a new encapsulating parameter in a classification, the facility displays the default parameters for the classification as proposed encapsulated parameters for the encapsulating parameters. The user may then delete any of the default parameters, and add any other desired encapsulated parameters to the created encapsulating parameters. Default parameters are useful in classifications such as medications, in which many drug parameters encapsulate the same encapsulated parameters, such as dose, dose units, and route.

In an additional preferred embodiment, the facility permits encapsulating parameters, as well as non-encapsulating result parameters, to be defined to contain result values. Those skilled in the art will recognize that the description of the facility described above may straightforwardly be adapted to enable encapsulating parameters to have result values. Such an adaptation merely requires the separation of data type and encapsulating information in the parameter definition table, which is discussed above in conjunction with FIG. 4; separate treatment of encapsulation and data type information in the parameter creation process, which is discussed above in conjunction with FIG. 5; and displaying an encapsulating parameter's result values instead of the result values of a primary encapsulated parameter of the encapsulating parameter beside the encapsulating parameter's name in a flowsheet, which is discussed above in conjunction with FIG. 8.

While this invention has been shown and described with reference to preferred embodiments, it will be understood by those skilled in the art that various changes or modifications in form and detail may be made without departing from the scope of the invention.

We claim:

1. A method in a computer system for designing, under the control of a user, a patient information hierarchy, the hierarchy containing a plurality of parameters including a linked-from parameter having a linked-from possible result value that is linked to one or more linked-to parameters, the method comprising the steps of:

(a) receiving an instruction from the user to create a new parameter within the patient information hierarchy;

(b) in response to step (a), creating a new parameter within the patient information hierarchy;

(c) receiving an instruction from the user to specify a plurality of indicated possible result values for the new parameter;

(d) in response to step (c), specifying the indicated possible result values as possible result values of the new parameter;

(e) receiving an instruction from the user to link an indicated linked-from possible result value among the possible result values of the new parameter to one or more indicated linked-to parameters contained within the patient information hierarchy; and (f) in response to step (e), within the patient information hierarchy, linking the indicated linked-from possible result value to the indicated linked-to parameters, such that the new parameter is a linked-from parameter, and such that, when the new parameter is displayed for a particular patient, if the new parameter has the linked-from possible result value, the linked-to parameters are displayed in conjunction with the new parameter.

2. The method of claim 1 wherein step (e) comprises the steps of:
   (e)(1) receiving an instruction from the user to link an indicated linked-from possible result value among the possible result values for the new parameter to other parameters within the patient information hierarchy;
   (e)(2) in response to step (e)(1), displaying a representation of the patient information hierarchy showing the parameters contained therein; and
   (e)(3) receiving one or more indications each indicating that an indicated parameter contained within the patient information hierarchy displayed in step (e)(2) has been selected as a linked-to parameter by the user.

3. The method of claim 1, further including the steps of, for a particular patient:
   displaying the linked-from parameter;
   receiving a result value for the linked-from parameter;
   determining whether the received result value is a linked-from possible result value; and
   in response to determining that the received result value is a linked-from possible result value, displaying each of the linked-to parameters that are linked to the linked-from possible result value.

4. A method in a computer system for designing, under the control of a user, a patient information hierarchy, the patient information hierarchy containing a plurality of parameters that may be displayed in conjunction with a particular patient, the parameters including both result parameters that may have a result value for each patient and encapsulating parameters that each identify and encapsulate one or more other parameters to represent them together at a higher conceptual level, the method comprising the steps of:
   (a) receiving an instruction to create a first result parameter that may have a result value for each patient, the instruction specifying a parameter name and a data type;
   (b) in response to step (a), creating within the patient information hierarchy a first result parameter having the parameter name and data type specified in the instruction received in step (a);
   (c) receiving an instruction to create a second result parameter that may have a result value for each patient, the instruction specifying a parameter name and a data type;
   (d) in response to step (c), creating within the patient information hierarchy a second result parameter having the parameter name and data type specified in the instruction received in step (c);
   (e) receiving an instruction to create a first encapsulating parameter and for encapsulating one or more other parameters to represent them together at a higher conceptual level, the instruction specifying a parameter name and a list of encapsulated parameters, the specified list of encapsulated parameters including the first result parameter and excluding the second result parameter;
   (f) in response to step (e), creating within the patient information hierarchy a first encapsulating parameter having the parameter name and the list of encapsulated parameters specified in the instruction received in step (e);
   (g) receiving an instruction to display the patient information hierarchy for a particular patient in a user-selected flowsheet, the user-selected flowsheet including the second result parameter and the first encapsulatory parameter; and
   (h) in response to step (g), displaying a list of parameters including the first encapsulating parameter and the second result parameter and excluding the first result parameter.

5. The method of claim 4, further including the steps of:
   (i) after step (h), receiving an instruction from the user to expand the first encapsulating parameter; and
   (j) in response to step (i), displaying the encapsulated parameters of the first encapsulating parameter, including the first result parameter, in conjunction with the first encapsulating parameter.

6. The method of claim 5, further including the steps of:
   (k) after step (j), receiving an instruction from the user to collapse the first encapsulating parameter; and
   (l) in response to step (k), displaying the first encapsulating parameter without the encapsulated parameters of the first encapsulating parameter, including the first result parameter.

7. The method of claim 4, further including the step of receiving an instruction to display the result value for a selected primary one of the list of encapsulated parameters of the first encapsulating parameter as the result value for the first encapsulating parameter, and wherein step (h) includes the step of displaying the result value for the selected primary encapsulated parameter as the result value for the first encapsulating parameter.

8. The method of claim 4 wherein the patient information hierarchy further includes a plurality of classifications each for grouping related parameters, each of the parameters in the patient information hierarchy being associated with one of the classifications, and wherein a set of default encapsulated parameters may be associated with each classification, and wherein step (e) includes the step of receiving an indication of a classification with which to associate the first encapsulating parameter, and wherein step (f) includes the step of defaulting the list of encapsulated parameters of the created first encapsulating parameter to contain the parameters in the set of default encapsulated parameters associated with the classification indicated by the received classification indication.

9. The method of claim 8, further including the step of permitting the user to override the default encapsulated parameters in the list of encapsulated parameters of the first encapsulating parameter.

10. A method in a computer system for designing and maintaining the contents of a patient information hierarchy comprised of a plurality of parameters that may contain result values for a particular patient, the patient information hierarchy having associated with it one or more flowsheets for displaying and modifying the result values of parameters for a particular patient, each flowsheet being comprised of one or more flowsheet groups that specify a subset of the parameters of the patient information hierarchy, the method comprising the steps of:
   (a) associating predetermined result values with a plurality of the parameters specified by a selected flowsheet group of a selected flowsheet;
   (b) receiving an instruction from the user to display the parameters specified by the selected flowsheet group of the selected flowsheet for a specified patient;
   (c) in response to step (b), displaying the parameters specified by the selected flowsheet group of the selected flowsheet for the specified patient;

(d) receiving an instruction from the user to set to the predetermined result values the result values for the specified patient of the displayed the parameters specified by the selected flowsheet group of the selected flowsheet; and (e) in response to step (d), for each parameter specified by the selected flowsheet group of the selected flowsheet with which a predetermined result value is associated, storing the predetermined result value in conjunction with the parameter for the specified patient.

11. A method in a computer system for designing and maintaining the contents of a plurality of named parameters identified by parameter identifiers that may contain result values for a particular patient, the parameters being arranged in a patient information hierarchy, the method comprising the steps of:

(a) receiving instructions from a user to create a parameter having a first name at a first location in the patient information hierarchy and a second location in the patient information hierarchy, the instructions further specifying that the parameter having the first name is a global parameter;

(b) in response to step (a), creating parameters at the first and second locations in the patient information hierarchy that are both identified by a first parameter identifier;

(c) receiving instructions from a user to create a parameter having a second name at a third location in the patient information hierarchy and a fourth location in the patient information hierarchy, the instructions further specifying that the parameter having the second name is a local parameter;

(d) in response to step (c), creating a parameter at the third location in the patient information hierarchy that is identified by a second parameter identifier and creating a parameter at the fourth location in the patient information hierarchy that is identified by a third parameter identifier, wherein the second and third parameter identifiers are distinct.

12. The method of claim 11 wherein each result value contained by a parameter is stored in a row of a result table containing the parameter identifier that identifies the parameter, further including the steps of:

(e) receiving a first result value for the parameter having the first name at the first location in the patient information hierarchy;

(f) in response to step (e), storing the first result value in a row of the result table containing the first parameter identifier;

(g) receiving a second result value for the parameter having the first name at the second location in the patient information hierarchy;

(h) in response to step (g), storing the second result value in a row of the result table containing the first parameter identifier;

(i) receiving a third result value for the parameter having the second name at the third location in the patient information hierarchy;

(j) in response to step (i), storing the third result value in a row of the result table containing the second parameter identifier;

(k) receiving a fourth result value for the parameter having the second name at the fourth location in the patient information hierarchy; and (l) in response to step (k), storing the fourth result value in a row of the result table containing the third parameter identifier.

13. The method of claim 12, further including the steps of:

(m) after step (e), receiving an instruction to display the result value for the parameter having the first name at the first location in the patient information hierarchy;

(n) in response to step (m), retrieving the first result value from the row of the result table containing the first parameter identifier;

(o) after step (g), receiving an instruction to display the result value for the parameter having the first name at the second location in the patient information hierarchy;

(p) in response to step (o), retrieving the second result value from a row of the result table containing the first parameter identifier;

(q) after step (i), receiving an instruction to display the result value for the parameter having the second name at the third location in the patient information hierarchy;

(r) in response to step (q), retrieving the third result value from a row of the result table containing the second parameter identifier;

(s) after step (k), receiving an instruction to display the result value for the parameter having the second name at the fourth location in the patient information hierarchy; and (t) in response to step (s), retrieving the fourth result value from a row of the result table containing the third parameter identifier.

14. A method in a computer system for designing and maintaining the contents of a patient information hierarchy comprised of a plurality of parameters that may contain result values for a particular patient, the patient information hierarchy having associated with it a flowsheet for displaying and modifying the result values of a subset of the parameters of the patient information hierarchy for a particular patient, the subset of the parameters that may be displayed and modified using the flowsheet including a parameter of a patient note type, having a result value comprising an author name field, a time field, and a note text field, the method comprising the steps of:

(a) receiving an instruction from the user to display parameter result values for a selected patient using the flowsheet;

(b) in response to step (a), displaying parameter result values for the selected patient using the flowsheet such that the result value of the parameter of the patient note type is displayed in an abbreviated form in conjunction with the other parameters in the subset, such that at least a portion of the author name field is displayed;

(c) receiving an indication that the user has selected the result value of the parameter of the patient note type is displayed in an abbreviated form; and (d) in response to step (c), displaying the entire contents of the result value of the parameter of the patient note type, such that the complete contents of the author name, time and note text fields are displayed.

15. A method in a computer system for designing and maintaining the contents of a patient information hierarchy comprised of a plurality of parameters that may contain result values for a particular patient, the patient information hierarchy having associated with it one or more flowsheets for displaying and modifying the result values of parameters for a particular patient, each flowsheet being comprised of one or more flowsheet groups that specify a subset of the parameters of the patient information hierarchy, a selected flowsheet group of a selected flowsheet further specifying a parameter placeholder not associated with any particular parameter, the method comprising the steps of:

(a) receiving an instruction from the user to display the parameters specified by the selected flowsheet group of the selected flowsheet for a specified patient;

(b) in response to step (a), displaying the parameters and the parameter placeholder specified by the selected flowsheet group of the selected flowsheet for the specified patient;

(c) receiving an instruction from the user to replace the parameter placeholder with a selected parameter of the patient information hierarchy;

(d) in response to step (c), replacing the parameter placeholder specified by the selected flowsheet group of the selected flowsheet for the specified patient with the selected parameter; and (e) after step (d), displaying the parameters specified by the selected flowsheet group of the selected flowsheet for the specified patient, including the selected parameter and excluding the parameter placeholder.

16. The method of claim 15, further including the steps of:

after step (d), receiving a result value for the selected parameter for the selected patient; and storing the received result value in conjunction with the selected parameter for the selected patient, and wherein step (e) includes the step of displaying the received result value in conjunction with the selected parameter.

17. The method of claim 15 wherein the parameter placeholder encapsulates an encapsulated parameter, and wherein step (b) also displays the encapsulated parameter.

18. The method of claim 15 wherein the parameter placeholder encapsulates a second parameter placeholder, and wherein step (b) also displays the second parameter placeholder, further including the steps of:

(f) receiving an instruction from the user to replace the second parameter placeholder with a second selected parameter of the patient information hierarchy;

(g) in response to step (f), replacing the second parameter placeholder with the second selected parameter; and (h) after step (g), displaying the parameters specified by the selected flowsheet group of the selected flowsheet for the specified patient, including the second selected parameter and excluding the second parameter placeholder.

19. The method of claim 15 wherein the selected parameter is an encapsulating parameter encapsulating one or more encapsulated parameters, and wherein step (e) includes the step of displaying the encapsulated parameters of the selected parameter.

20. The method of claim 15 wherein a list of a plurality of parameters of the hierarchy that may be substituted for the parameter placeholder is associated with the parameter placeholder, and wherein step (c) includes the steps of:

displaying the list of parameters that may be substituted for the parameter placeholder; and receiving input indicating that the user has selected the selected parameter from the displayed list.

21. A method in a computer system for designing, under the control of a user, a patient information hierarchy, the hierarchy containing a plurality of parameters that may each have a result value for each patient, the hierarchy further containing a plurality of classifications each for grouping related parameters, each of the parameters in the patient information hierarchy being associated with one of the classifications, and wherein the patient information hierarchy has associated with it one or more flowsheets for displaying and modifying the result values of parameters for a particular patient, each flowsheet being comprised of one or more flowsheet groups that specify a subset of the parameters of the patient information hierarchy, the method comprising the steps of, in response to a step of receiving an instruction from the user to create a new parameter:

(a) prompting the user for the name of a new parameter;

(b) receiving from the user the name of a new parameter;

(c) prompting the user to identify the classification with which the new parameter should be associated;

(d) receiving from the user an indication of the classification with which the new parameter should be associated;

(e) prompting the user to select the data type of the new parameter;

(f) receiving from the user an indication of the data type of the new parameter;

(g) creating in the patient information hierarchy a new parameter that has the received name, that is associated with the indicated classification, and that has the indicated data type;

(h) displaying the parameters specified by a selected flowsheet group of a selected flowsheet in conjunction with their result values for a selected patient, the displayed parameters excluding the new parameter;

(i) receiving an instruction from the user to add a parameter to the selected flowsheet group of the selected flowsheet;

(j) in response to step (i), displaying a portion of the patient information hierarchy including the name of the new parameter;

(k) receiving an instruction from the user selecting the displayed name of the new parameter;

(l) in response to step (k), adding the new parameter to the selected flowsheet group of the selected flowsheet; and (m) in response to step (l), displaying the new parameter among the parameters specified by a selected flowsheet group of a selected flowsheet in conjunction with their result values for a selected patient.

22. The method of claim 21 wherein step (e) includes the step of prompting the user to select the data type of the new parameter from a plurality of available data types, and wherein the plurality of data types includes a selection data type, parameters of which may contain one of a predefined set of possible result values, and further including the steps of, if the indication of the data type of the new parameter received in step (f) indicates the selection data type:

(h) prompting the user to input the set of possible result values for the new parameter; and (i) receiving from the user the set of possible result values for the new parameter, and wherein step (g) creates a new parameter having the received set of possible result values.

23. The method of claim 21 wherein step (e) includes the step of prompting the user to select the data type of the new parameter from a plurality of available data types, and wherein the plurality of data types includes a calculated data type, parameters of which may contain a formula based on the result values of other parameters, and further including the steps of, if the indication of the data type of the new parameter received in step (f) indicates the selection data type:

(h) prompting the user to input the formula for the new parameter; and (i) receiving from the user the formula for the new parameter, and wherein step (g) creates a new parameter having the received formula.

24. The method of claim 21 wherein step (c) includes the step of displaying a list of the plurality of classifications, and wherein step (d) includes the step of receiving an indication that the user has selected a particular one of the classifications in the displayed list, and wherein step (e) includes the step of displaying a list of available data types, and wherein step (f) includes the step of receiving an indication that the user has selected a particular one of the available data types in the displayed list.

25. The method of claim 10 wherein the associating step associates with the plurality of the parameters specified by the selected flowsheet group of the selected flowsheet normal result values for these parameters.

* * * * *